(12) United States Patent
Cronin et al.

(10) Patent No.: US 9,474,933 B1
(45) Date of Patent: Oct. 25, 2016

(54) PROFESSIONAL WORKOUT SIMULATOR

(71) Applicant: ProSports Technologies, LLC, Miami, FL (US)

(72) Inventors: John E. Cronin, Bonita Springs, FL (US); Nick Reasner, Chicago, IL (US)

(73) Assignee: ProSports Technologies, LLC, Miami, FL (US)

( * ) Notice: Subject to any disclaimer, the term of this patent is extended or adjusted under 35 U.S.C. 154(b) by 0 days.

(21) Appl. No.: 14/798,057

(22) Filed: Jul. 13, 2015

Related U.S. Application Data

(60) Provisional application No. 62/023,472, filed on Jul. 11, 2014.

(51) Int. Cl.
*A63B 24/00* (2006.01)

(52) U.S. Cl.
CPC .................................. *A63B 24/0075* (2013.01)

(58) Field of Classification Search
USPC .......................................................... 700/91
See application file for complete search history.

(56) References Cited

U.S. PATENT DOCUMENTS

| | | | |
|---|---|---|---|
| 4,763,284 A | 8/1988 | Carlin | |
| 4,771,394 A | 9/1988 | Cavanagh | |
| 5,293,354 A | 3/1994 | Costabile | |
| 5,462,275 A | 10/1995 | Lowe et al. | |
| 6,013,007 A | 1/2000 | Root et al. | |
| 6,181,236 B1 | 1/2001 | Schneider | |
| 6,389,368 B1 | 5/2002 | Hampton | |
| 6,603,711 B2 | 8/2003 | Calace | |
| 6,760,276 B1 | 7/2004 | Karr | |
| 6,836,744 B1 | 12/2004 | Asphahani et al. | |
| 7,020,336 B2 | 3/2006 | Cohen-Solal et al. | |
| 7,031,225 B2 | 4/2006 | McDonald | |
| 7,115,053 B2 | 10/2006 | Meichner | |
| 7,173,533 B1 | 2/2007 | Beron et al. | |
| 7,174,277 B2 | 2/2007 | Vock et al. | |
| 7,561,494 B2 | 7/2009 | Stern | |
| 7,561,723 B2 | 7/2009 | Goldberg et al. | |
| 7,602,301 B1 | 10/2009 | Stirling et al. | |
| 7,618,312 B1 | 11/2009 | Kasten | |
| 7,634,662 B2 | 12/2009 | Monroe | |

(Continued)

FOREIGN PATENT DOCUMENTS

| AU | 2014100006 | 2/2014 |
|---|---|---|
| CN | 102527007 | 7/2012 |

(Continued)

OTHER PUBLICATIONS

"About Head Case", Head Case Company, Sep. 24, 2013.

(Continued)

*Primary Examiner* — Pierre E Elisca
(74) *Attorney, Agent, or Firm* — Polsinelli LLP

(57) ABSTRACT

The systems and methods described herein are directed towards collecting workout-based information from professional athletes and providing the collected workout-based information to users. The workout-based information of the professional athletes are collected through the use of wearable devices and stored in a workout-based information network. The users (e.g., fans, other professional athletes) may subsequently download workout-based data of one or more professional athletes onto their user device. The workout-based data may be used by the users to compare their own personal progress with the professional athletes.

13 Claims, 4 Drawing Sheets

(56) References Cited

U.S. PATENT DOCUMENTS

| | | | |
|---|---|---|---|
| 7,693,668 B2 | 4/2010 | Vock et al. |
| 7,715,723 B2 | 5/2010 | Kagawa et al. |
| 7,805,149 B2 | 9/2010 | Werner et al. |
| 7,920,052 B2 | 4/2011 | Costabile |
| 8,054,174 B1 | 11/2011 | Uehran |
| 8,098,881 B2 | 1/2012 | Camp et al. |
| 8,239,146 B2 | 8/2012 | Vock et al. |
| 8,253,586 B1 | 8/2012 | Matak |
| 8,257,084 B1 | 9/2012 | Kreiner et al. |
| 8,257,228 B2 | 9/2012 | Quatrochi et al. |
| 8,289,185 B2 | 10/2012 | Alonso |
| 8,326,136 B1 | 12/2012 | Clark |
| 8,396,687 B2 | 3/2013 | Vock et al. |
| 8,477,046 B2 | 7/2013 | Alonso |
| 8,485,879 B2 | 7/2013 | Lin et al. |
| 8,554,495 B2 | 10/2013 | Mack et al. |
| 8,554,509 B2 | 10/2013 | Crisco et al. |
| 8,579,632 B2 | 11/2013 | Crowley |
| 8,589,667 B2 | 11/2013 | Mujtaba et al. |
| 8,611,930 B2 | 12/2013 | Louboutin et al. |
| 8,620,344 B2 | 12/2013 | Huang et al. |
| 8,626,465 B2 | 1/2014 | Moore et al. |
| 8,630,216 B2 | 1/2014 | Deivasigamani et al. |
| 8,660,501 B2 | 2/2014 | Sanguinetti |
| 8,684,819 B2 | 4/2014 | Thomas et al. |
| 8,702,504 B1 | 4/2014 | Hughes et al. |
| 8,706,044 B2 | 4/2014 | Chang et al. |
| 8,724,723 B2 | 5/2014 | Panicker et al. |
| 8,750,207 B2 | 6/2014 | Jeong et al. |
| 8,793,094 B2 | 7/2014 | Tam et al. |
| 8,816,868 B2 | 8/2014 | Tan et al. |
| 8,831,529 B2 | 9/2014 | Toh et al. |
| 8,831,655 B2 | 9/2014 | Burchill et al. |
| 8,836,851 B2 | 9/2014 | Brunner |
| 8,843,158 B2 | 9/2014 | Nagaraj |
| 8,849,308 B2 | 9/2014 | Marti et al. |
| 8,862,060 B2 | 10/2014 | Mayor |
| 8,873,418 B2 | 10/2014 | Robinson et al. |
| 8,874,090 B2 | 10/2014 | Abuan et al. |
| 8,917,632 B2 | 12/2014 | Zhou et al. |
| 8,934,921 B2 | 1/2015 | Marti et al. |
| 8,994,498 B2 | 3/2015 | Agrafioti et al. |
| 9,305,441 B1 | 4/2016 | Cronin |
| 9,398,213 B1 | 7/2016 | Cronin |
| 2001/0003715 A1 | 6/2001 | Jutzi et al. |
| 2001/0048484 A1 | 12/2001 | Tamir et al. |
| 2003/0163287 A1 | 8/2003 | Vock et al. |
| 2003/0210612 A1 | 11/2003 | Stern |
| 2005/0046584 A1 | 3/2005 | Breed |
| 2005/0117022 A1 | 6/2005 | Marchant |
| 2005/0162257 A1 | 7/2005 | Gonzalez |
| 2005/0242508 A1 | 11/2005 | Meichner |
| 2005/0277466 A1 | 12/2005 | Lock |
| 2006/0052147 A1 | 3/2006 | Matthews |
| 2006/0109089 A1 | 5/2006 | Boehm et al. |
| 2006/0180073 A1 | 8/2006 | Nakamoto |
| 2006/0208169 A1 | 9/2006 | Breed et al. |
| 2006/0281061 A1 | 12/2006 | Hightower et al. |
| 2007/0003113 A1 | 1/2007 | Goldberg |
| 2007/0135264 A1 | 6/2007 | Rosenberg |
| 2007/0269203 A1 | 11/2007 | Awazu |
| 2008/0082311 A1 | 4/2008 | Meijer et al. |
| 2008/0129825 A1 | 6/2008 | DeAngelis et al. |
| 2008/0146302 A1 | 6/2008 | Olsen et al. |
| 2009/0023122 A1 | 1/2009 | Lieberman et al. |
| 2009/0029754 A1 | 1/2009 | Slocum et al. |
| 2009/0111582 A1 | 4/2009 | Schuler et al. |
| 2009/0256912 A1 | 10/2009 | Rosenberg |
| 2010/0026809 A1 | 2/2010 | Curry |
| 2010/0030350 A1 | 2/2010 | House et al. |
| 2010/0102938 A1 | 4/2010 | Delia et al. |
| 2010/0105503 A1 | 4/2010 | Daisher et al. |
| 2010/0144414 A1 | 6/2010 | Edis et al. |
| 2010/0185398 A1 | 7/2010 | Berns et al. |
| 2010/0283630 A1 | 11/2010 | Alonso |
| 2011/0013087 A1 | 1/2011 | House et al. |
| 2011/0064281 A1 | 3/2011 | Chan |
| 2011/0169959 A1 | 7/2011 | DeAngelis et al. |
| 2011/0181418 A1 | 7/2011 | Mack et al. |
| 2011/0184320 A1 | 7/2011 | Shipps et al. |
| 2012/0002509 A1 | 1/2012 | Saguin et al. |
| 2012/0029666 A1 | 2/2012 | Crowley et al. |
| 2012/0052947 A1 | 3/2012 | Yun |
| 2012/0063272 A1 | 3/2012 | Dorais et al. |
| 2012/0081531 A1 | 4/2012 | DeAngelis et al. |
| 2012/0099405 A1 | 4/2012 | Lidor et al. |
| 2012/0116548 A1 | 5/2012 | Goree et al. |
| 2012/0120201 A1 | 5/2012 | Ward |
| 2012/0124720 A1 | 5/2012 | Evans et al. |
| 2012/0166449 A1 | 6/2012 | Pitaliya |
| 2012/0197998 A1 | 8/2012 | Kessel et al. |
| 2012/0202594 A1 | 8/2012 | Bistis et al. |
| 2012/0212505 A1 | 8/2012 | Burroughs et al. |
| 2012/0223833 A1 | 9/2012 | Thomas et al. |
| 2012/0324491 A1 | 12/2012 | Bathiche et al. |
| 2013/0018494 A1 | 1/2013 | Amini |
| 2013/0045806 A1 | 2/2013 | Bloodworth |
| 2013/0060168 A1 | 3/2013 | Chu et al. |
| 2013/0066448 A1 | 3/2013 | Alonso |
| 2013/0080222 A1 | 3/2013 | Quinn |
| 2013/0091209 A1 | 4/2013 | Bennett et al. |
| 2013/0095924 A1 | 4/2013 | Geisner et al. |
| 2013/0126713 A1 | 5/2013 | Haas et al. |
| 2013/0138590 A1 | 5/2013 | Huke et al. |
| 2013/0139068 A1 | 5/2013 | Bowring |
| 2013/0141555 A1 | 6/2013 | Ganick et al. |
| 2013/0166048 A1 | 6/2013 | Werner et al. |
| 2013/0222133 A1 | 8/2013 | Schultz et al. |
| 2013/0235702 A1 | 9/2013 | Saguin et al. |
| 2013/0249708 A1* | 9/2013 | Moll-Carrillo .... A63B 24/0062 340/870.02 |
| 2013/0279917 A1 | 10/2013 | Son et al. |
| 2013/0303192 A1 | 11/2013 | Louboutin |
| 2013/0316837 A1 | 11/2013 | Coiner, Jr. |
| 2013/0317835 A1 | 11/2013 | Mathew |
| 2013/0322689 A1 | 12/2013 | Carmichael |
| 2013/0324239 A1 | 12/2013 | Ur et al. |
| 2013/0328917 A1 | 12/2013 | Zambetti et al. |
| 2013/0331087 A1 | 12/2013 | Shoemaker |
| 2013/0331118 A1 | 12/2013 | Chhabra |
| 2013/0331137 A1 | 12/2013 | Burchill |
| 2013/0332108 A1 | 12/2013 | Patel |
| 2013/0332156 A1 | 12/2013 | Tackin |
| 2013/0335635 A1 | 12/2013 | Ghanem et al. |
| 2013/0336662 A1 | 12/2013 | Murayama et al. |
| 2013/0343762 A1 | 12/2013 | Murayama et al. |
| 2014/0004939 A1 | 1/2014 | Kasten |
| 2014/0039354 A1 | 2/2014 | Greenwald et al. |
| 2014/0039355 A1 | 2/2014 | Crisco et al. |
| 2014/0039651 A1 | 2/2014 | Crowley |
| 2014/0062773 A1 | 3/2014 | MacGougan |
| 2014/0065962 A1 | 3/2014 | Le |
| 2014/0068847 A1 | 3/2014 | Kitowski |
| 2014/0071221 A1 | 3/2014 | Dave |
| 2014/0080638 A1 | 3/2014 | Feng et al. |
| 2014/0088454 A1 | 3/2014 | Mack |
| 2014/0105084 A1 | 4/2014 | Chhabra |
| 2014/0105466 A1 | 4/2014 | Botes et al. |
| 2014/0107817 A1* | 4/2014 | Ellis .................... A61B 5/1038 700/91 |
| 2014/0111352 A1 | 4/2014 | Doherty |
| 2014/0125702 A1 | 5/2014 | Santillan et al. |
| 2014/0139380 A1 | 5/2014 | Ouyang |
| 2014/0141803 A1 | 5/2014 | Marti |
| 2014/0143940 A1 | 5/2014 | Luliano et al. |
| 2014/0155178 A1 | 6/2014 | Bloodworth |
| 2014/0162628 A1 | 6/2014 | Bevelacqua |
| 2014/0167794 A1 | 6/2014 | Nath |
| 2014/0168170 A1 | 6/2014 | Lazarescu |
| 2014/0168477 A1 | 6/2014 | David |
| 2014/0171114 A1 | 6/2014 | Marti |
| 2014/0180820 A1 | 6/2014 | Louboutin |
| 2014/0191979 A1 | 7/2014 | Tsudik |
| 2014/0200053 A1 | 7/2014 | Balasubramanian |

(56) References Cited

U.S. PATENT DOCUMENTS

| | | | |
|---|---|---|---|
| 2014/0218184 A1 | 8/2014 | Grant et al. | |
| 2014/0222335 A1 | 8/2014 | Piemonte | |
| 2014/0232633 A1 | 8/2014 | Shultz | |
| 2014/0232634 A1 | 8/2014 | Piemonte | |
| 2014/0241730 A1 | 8/2014 | Jovicic et al. | |
| 2014/0247279 A1 | 9/2014 | Nicholas | |
| 2014/0247280 A1 | 9/2014 | Nicholas | |
| 2014/0269562 A1 | 9/2014 | Burchill | |
| 2014/0270375 A1 | 9/2014 | Canavan et al. | |
| 2014/0274150 A1 | 9/2014 | Marti | |
| 2014/0278218 A1 | 9/2014 | Chang | |
| 2014/0283135 A1 | 9/2014 | Shepherd | |
| 2014/0293959 A1 | 10/2014 | Singh | |
| 2014/0361906 A1 | 12/2014 | Hughes et al. | |
| 2014/0363168 A1 | 12/2014 | Walker | |
| 2014/0364089 A1 | 12/2014 | Lienhart | |
| 2014/0364148 A1 | 12/2014 | Block | |
| 2014/0365120 A1 | 12/2014 | Vulcano | |
| 2014/0365640 A1 | 12/2014 | Wohl et al. | |
| 2014/0371887 A1* | 12/2014 | Hoffman | G06K 9/00342 700/91 |
| 2014/0375217 A1 | 12/2014 | Feri et al. | |
| 2015/0011242 A1 | 1/2015 | Nagaraj | |
| 2015/0026623 A1 | 1/2015 | Horne et al. | |
| 2015/0031397 A1 | 1/2015 | Jouaux | |
| 2015/0081713 A1 | 3/2015 | Alonso et al. | |
| 2015/0131845 A1 | 5/2015 | Forouhar et al. | |
| 2015/0187188 A1 | 7/2015 | Raskin | |
| 2015/0296272 A1 | 10/2015 | Sonabend et al. | |
| 2015/0306457 A1* | 10/2015 | Crankson | G06K 9/00342 700/91 |
| 2016/0001159 A1* | 1/2016 | Riley | A63B 24/0006 700/91 |
| 2016/0008693 A1 | 1/2016 | Cronin | |
| 2016/0012810 A1 | 1/2016 | Cronin | |
| 2016/0073010 A1 | 3/2016 | Cronin | |
| 2016/0096074 A1* | 4/2016 | Moll-Carrillo | A63B 24/0062 715/772 |
| 2016/0107064 A1* | 4/2016 | Hoffman | A63B 24/0084 700/91 |

FOREIGN PATENT DOCUMENTS

| | | |
|---|---|---|
| CN | 102843186 | 12/2012 |
| EP | 2 407 218 | 1/2012 |
| WO | WO 2008/030484 | 3/2008 |
| WO | WO 2009/104921 | 8/2009 |
| WO | WO 2011/004381 | 1/2011 |
| WO | WO 2012/100053 | 7/2012 |
| WO | WO 2013/011259 | 1/2013 |
| WO | WO 2013/166456 | 11/2013 |
| WO | WO 2014/008134 | 1/2014 |
| WO | WO 2014/052874 | 4/2014 |
| WO | WO 2014/100519 | 6/2014 |
| WO | WO 2016/007969 | 1/2016 |
| WO | WO 2016/007970 | 1/2016 |
| WO | WO 2016/039991 | 3/2016 |

OTHER PUBLICATIONS

"Adidas' miCoach SPEED_CELL and miCoach Football App Aim to Advance the Performance of Next-Generation Athletes Through New Technology", miCoach, Nov. 22, 2011.
"Advanced E-Team: Automatic Sports Time Stopping Whistle", Rose-Hulman Institute of Technology, 2002, NCIIA Funded Advanced E-Teams. Date of Download: Jun. 14, 2014. http://www.nciia.org/WebObjects/NciiaResources.woa/wa/View/GrantProfile?n=1000037.
"Affordable Concussion Management System for Young Athletes Offered by Head Case", Head Case Company, Sep. 24, 2013.
Ancona et al., N.; "Goal detection in football by using Support Vector Machines for classification" Neural Networks, vol. 1, pp. 611-616, 2001.
"AutoScout" ADSC Illinous at Singapore Pte Ltd. Sep. 21, 2015.
Belzer, Jason; "NFL Partners With Zebra Technologies to Provide Next Generation Player Tracking", Forbes/Sports Money, Jul. 31, 2014.
Brolinson et al., P. Gunner; "Analysis of Linear Head Accelerations from Collegiate Football Impacts", Current Sports Medicine Reports, 2006, vol. 5:23-28.
"Chapter 29. Outdoor Laser Operations", U.S. Department of Transportation, Feb. 9, 2012.
Cooley, Chris; "MMQB: Smart Football", The Official Blog of Chris Cooley, Jul. 13, 2009.http://chriscooley47.blogspot.com/2009/07/mmqb-smart-football.html.
"Create Innovative Services with Play Apps", Date of Download: Jan. 16, 2014, http://www.oledcomm.com/LIFI.html, Oledcomm—France LiFi.
Danakis, C et al.; "Using a CMOS Camera Sensor for Visible Light Communication"; 3rd IEEE Workshop on Optical Wireless Communications; [online], Dec. 3-7, 2012 [retrieved Aug. 14, 2015]. Retrieved from the Internet: <URL: https://195.134.65.236/IEEE_Globecom_2012/papers/p1244-danakis.pdf> pp. 1244-1248.
Dawson, Keith; "LiFi in the Real World" All LED Lighting—Illuminating the Led Community, Jul. 31, 2013.
Delgado, Rick; "Why Fantasy Football is Embracing Big Data", Sporttechie, Jan. 3, 2014.
"Dutch Football Fans Get the Ajax Experience With AV Technology From Electrosonic", Electrosonic Press Release, May 14, 2012.
FAQ, Go Pro Workouts, Date of Download: Apr. 30, 2014 https://www.goproworkouts.com/faqs.
"First Down Laser Systems to enhance game of football and fans in-stadium experience with green line", Sports Techie, Sep. 9, 2013.
"Football Workout Programs", Go Pro Workouts. Date of Download: Apr. 27, 2014 https://www.goproworkouts.com/workouts/football.
Freeman, Mark; "Frickin' Laser Beams", River Valley Leader, Feb. 19, 2013.
Gerhardt, Ryan; "Concussion Sensing Helmet Could Save Athletes", PSFK, Oct. 28, 2013.
Gerhardt, Ryan; "Vibrating Jersey Lets Fans Feel What Players Do on the Field", PSFK.com, Mar. 13, 2014.
"GoalControl to provide goal-line system at World Cup in Brazil", BBC Sport, Apr. 2, 2013.
Gorman, Michael; "Outstanding Technology brings visible light communication to phones and tablets via dongle and LEDs", Edgadget International Editions, Jul. 16, 2012.
"Growing data sets alter Sportsvision's real-time viewing experience", Sports Illustrated, More Sports, Nov. 29, 2013.
Haas, Harald; "Delivering safe and secure wireless communications", pureLiFi. Date of download: Jan. 16, 2014 http://purelifi.co.uk/.
"How to compare personal stats with the Pros?", Support Home Discussions Training with miCoach. Jul. 4, 2012.
"How to wear the Stride Sensor (inside the shoe)", by micoach, Guides & Tutorials, May 29, 2014.
Inamoto et al., Naho; "Immersive Observation of Virtualized Soccer Match at Real Stadium Model", Proceedings of the Second IEEE and ACM International Symposium on Mixed and Augmented Reality (ISMAR '03), 2003.
"Intel, NFL Legend Jerry Rice and others Team Up to "Look Inside the Huddle" On and Off the Field", by INTELPR in Intel Newsroom, Aug. 28, 2013.
Kumar, Navin; "Visible Light Communications Systems Conception and VIDAS", IETE Technical Review, vol. 25, Issue 6, Nov.-Dec. 2008. Date of download: Nov. 19, 2009. http://www.tr.ietejournals.org.
La Confora, Jason; "NFL collecting data that could revolutionize websites, video games", CBS Sports—Insider, Nov. 25, 2012.
Laviers, Kennard R.; Sukthankar, Gita; "Using Opponent Modeling to Adapt Team Play in American Football", Plan, Activity, and Recognition, Elsevier, 2014. School of ECE, Air Force Institute of Technology. Preprint submitted: Oct. 31, 2013.
LiFi Overview—Green wireless mobile communication—LiFi Technology. Date of download: Jan. 16, 2014.

(56) References Cited

OTHER PUBLICATIONS

Li, Yang et al., "VICO: A Framework for Configuring Indoor Visible Light Communication Networks" Aug. 11, 2012, Mobile Adhoc and Sensor Systems (MASS), 2012 IEEE 9th International Conference, Las Vegas, NV.
Macleod, Robert; "New football helmet sensors monitor brain injuries", The Globe and Mail, Nov. 14, 2013.
Madden, Lance; "Pro Athletes Share Personal Workout Secrets With Startup 'Go Pro Workouts'", Forbes.com, SportsMoney. Mar. 4, 2013.
Maricle, Charles; "Federal rules for outdoor laser user in the U.S. (FAA authority over airspace)", Laser PointerSafety.com, Apr. 23, 2014.
"Methods to Our Madness", Football Outsiders Information, Innovative Statistics, Intelligent Analysis, http://www.footballoutsiders.com/info/methods, Date of Download: Apr. 10, 2014.
Miller, Mark J.; "NFL Sensors Will Track Player Stats for Fans, but What About Safety?", Sports in the Spotlight—brandchannel, Aug. 11, 2014.
Montero, Eric, "Design and Implementation of Color-Shift Keying for Visible Light Communications", Sep. 2013, McMaster University.
Morgan, Debra; "Referee Uses Capital Idea to Stop Game Clocks on a Whistle", Loca News. Nov. 18, 1999. http://www.wral.com/news/local/story/138889.
Naidu, Vinaya; "Watched the IPL? Now Find and Tag Yourself in the Stadium With Vodafone Fancam", Business 2 Community, May 22, 2013.
"New courtside technology unveiled at PISD tourney", Precision Time Systems—New Inventions That Prevent Human Errors in Sports Timekeeping, Date of Download: Apr. 23, 2014.
Nguyen et al., "A Novel like switching scheme using pre-scanning and RSS prediction in visible light communication networks", EURASIP Journal on Wireless Communications and Networking, 2013.
"Nike+ SportBand User's Guide", by nikeplus.com, Jun. 7, 2014.
"Nokia Lumia 920 pricing compared to iPhone 5 and Samsung Galaxy SIII", by Nokia, Sep. 30, 2012.
Ogawa; "Article about VLC Guidance developed", Visible Light Communications Consortium (VLCC), Aug. 31, 2012.
Ogawa; "iPhone app from CASIO", Visible Light Communications Consortium (VLCC), Apr. 26, 2012.
Ogus, Simon; "SportIQ Announces a Game Changing Real-Time Basketball Analytics Platform", Sporttechie.com, Mar. 7, 2014.
"Omega introduces new timing equipment for ice hockey at Sochi 2014 Olympic Winter Games", OMEGA Watches, Feb. 16, 2014.
"Outdoor Laser Operations", Advisory Circular, U.S. Department of Transportation, Dec. 30, 2014.
Perin et al., Charles; "Real-Time Crowdsourcing of Detailed Soccer Data", IEEE, Oct. 2013.
Povey, Gordon, "VLC for Location, positioning and navigation", Jul. 27, 2011, http://visiblelightcomm.com/vlc-for-location-positioning-and-n . . . .
"Riddell InSite Impact Response System", Riddell InSite. Oct. 18, 2013.
Roble, Bob; "Inside the Huddle: How Big Data is Unlocking Fantasy Football Insights", IQ Sports—Sports Technology, Sep. 3, 2013.
Saag, Tonis; "You can compare your training data with friends again", SportlyzerBlog, Feb. 20, 2013.
"What is SafeBrain", SafeBrain Systems Inc. May 14, 2014.
Schoonmaker, Aaron; "NCAA ignoring own clock recommendations in tourney", WRALSportsFan.com, Mar. 25, 2014 http://www.wralsportsfan.com/ncaa-ignoring-own-clock-recommendations-in-tourney/13510770/.
"Smartabase—The complete solution for athlete data management", Fusion Sport, www.fusionsport.com, Jul. 21, 2011.

"Sports Event Services—Quality Information is the first gold medal at any event", Infostrada Sports, May 24, 2013.
Stein, Anne; "Devices help alert teams to potential concussions on the field", Tribune Newspapers, Jun. 27, 2012.
Thanigavel, M.; "Li-Fi Technology in Wireless Communication", International Journal of Engineering Research & Technology (IJERT), ISSN: 2278-0181, vol. 2 Issue 10, Oct. 2013.
"The Head Case Impact Sensor", Head Case Company, Sep. 24, 2013.
"The System Models & How They Work", Precision Time Systems—New Inventions That Prevent Human Errors in Sports Timekeeping, Date of Download: Apr. 24, 2014.
"The Wearables Coaching an Optimal Version of You", by PSFK Labs, iQ, Feb. 24, 2014.
"Train like professional athletes", Go Pro Workouts. Date of Download: Apr. 30, 2014 https://www.goproworkouts.com/.
"Viewing other miCoach stats", Support Home Discussions Training with miCoach, Jun. 26, 2012.
WKO—Hunter Allen—Peaks Coaching Group Oct. 14, 2015.
"Wirless Whistle System", Bodet Sport, Sport Display—Timer. Date of Download: Jun. 23, 2014 file:///Cl/king/AOP/Wireless%20Whistle%20system.htm[Jun. 23, 2014 7:32:06 PM].
Won, Eun Tae; "Visible Light Communication: Tutorial", Project: IEEE P802.15 Working Group for Wireless Personal Area Networks (WPANs), Mar. 9, 2008.
"Link: Would You Like to See the Goal-Post Lengthened in Height in College Football", TideFans.com, May 6, 2014. http://www.tidefans.com/forums/showthread.php?t=222422&page=4.
PCT Application No. PCT/US2015/033613 International Search Report and Written Opinion mailed Sep. 1, 2015.
PCT Application No. PCT/US2015/040228 International Search Report and Written Opinion mailed Sep. 30, 2015.
PCT Application No. PCT/US2015/040229 International Search Report and Written Opinion mailed Oct. 1, 2015.
PCT Application No. PCT/US2015/047059 International Search Report and Written Opinion mailed Nov. 9, 2015.
U.S. Appl. No. 14/798,049 Office Action mailed Nov. 3, 2015.
U.S. Appl. No. 14/798,081 Office Action mailed Sep. 28, 2015.
U.S. Appl. No. 14/798,091 Office Action mailed Sep. 22, 2015.
U.S. Appl. No. 14/788,728 Office Action mailed Sep. 17, 2015.
U.S. Appl. No. 14/788,742 Office Action mailed Sep. 2, 2015.
U.S. Appl. No. 15/091,139, John E. Cronin, Sensor Experience Garment, filed Apr. 5, 2016.
U.S. Appl. No. 14/798,049 Final Office Action mailed Mar. 22, 2016.
U.S. Appl. No. 14/798,091 Office Action mailed Mar. 28, 2016.
U.S. Appl. No. 14/798,035 Office Action mailed Nov. 24, 2015.
U.S. Appl. No. 14/798,068 Office Action mailed Nov. 23, 2015.
U.S. Appl. No. 14/798,131 Office Action mailed Jan. 12, 2016.
U.S. Appl. No. 14/798,204 Office Action mailed Jan. 22, 2016.
U.S. Appl. No. 14/798,190 Office Action mailed Jan. 12, 2016.
U.S. Appl. No. 14/829,598 Office Action mailed Feb. 2, 2016.
U.S. Appl. No. 14/788,728 Final Office Action mailed Feb. 1, 2016.
U.S. Appl. No. 14/788,742 Final Office Action mailed Jan. 6, 2016.
U.S. Appl. No. 14/798,068 Final Office Action mailed May 5, 2016.
U.S. Appl. No. 14/798,131 Final Office Action mailed May 23, 2016.
U.S. Appl. No. 14/798,204 Final Office Action mailed May 11, 2016.
U.S. Appl. No. 14/788,742 Office Action mailed May 11, 2016.
U.S. Appl. No. 15/187,100, filed Jun. 20, 2016, John E. Cronin, Smart Field Goal Detector.
U.S. Appl. No. 14/798,091 Office Action mailed Aug. 8, 2016.
U.S. Appl. No. 14/798,190 Final Office Action mailed Jul. 25, 2016.
U.S. Appl. No. 14/829,598 Final Office Action mailed Jul. 18, 2016.
U.S. Appl. No. 14/788,728 Office Action mailed Jul. 13, 2016.

* cited by examiner

PROFESSIONAL WORKOUT SIMULATOR

CROSS-REFERENCE TO RELATED APPLICATIONS

The present application claims the priority benefit of U.S. provisional application No. 62/023,472 filed Jul. 11, 2014 and entitled "Workout like a Pro," the disclosure of which is incorporated herein by reference.

BACKGROUND OF THE INVENTION

1. Field of Invention

The present invention generally relates to wearable devices. More specifically, the present invention relates to providing users with workout-based information from one or more professional athletes for comparison.

2. Description of the Related Art

Wearable technology may include any type of mobile electronic device that can be worn on the body, attached to or embedded in clothes and accessories of an individual and currently exist in the consumer marketplace. Processors and sensors associated with the wearable technology can display, process or gather information. Such wearable technology has been used in a variety of areas, including monitoring health data of the user as well as other types of data and statistics. These types of devices may be readily available to the public and may be easily purchased by consumers. Examples of some wearable technology in the health arena include Fit Bit, Nike Fuel Band, and the Apple Watch.

Professional athletes may utilize wearable technology to track their own personal progress during workouts. Through the use of wearable technology, professional athletes can monitor health-based data including number of calories burned, steps taken, and pulse/heart rate. The use of this information for each athlete may be beneficial to ensure that each professional athlete undertakes the necessary preparations so that they are prepared for their respective sports.

Presently there is no available way for fans to obtain access to the workout-based data of one or more professional athletes. Users of wearable devices are interested in comparing their own personal workout-based results with one or more pros. In some cases, professional athletes may also be interested in comparing their personal workout-based results with other professional athletes.

SUMMARY OF THE CLAIMED INVENTION

A method for comparing workout-based information between a user and one or more professional athletes is claimed. The method first stores workout-based information from one or more professional athletes in a workout-based network. Users can then select one or more of the workout-based information of professional athletes stored in the network to be downloaded. The users download the workout-based information of the selected professional athletes onto their user device. The users also provide their user workout-based information. The user device then evaluates the workout-based information of the user and the user selected professional athletes. The user device finally outputs information comparing the workout-based information of the user and user selected professional athletes onto a display that the user can view.

A system for comparing workout-based information between a user and one or more professional athletes is also claimed. The system includes a user interface, a database, and a processor. The database stores workout-based information of one or more professional athletes in a workout-based network. The processor executes instructions stored in memory to select one or more professional athletes having stored workout-based information associated with the workout-based network. The processor can then download the stored workout-based information of the user selected professional athletes and subsequently receive the user workout-based information. Evaluation of the workout-based information of the user and the professional athletes is performed in order to output information comparing the workout-based information of the user and user selected professional athletes. The information can be displayed for the user to view

DETAILED DESCRIPTION

The systems and methods described herein are directed towards collecting workout-based information from professional athletes and providing the collected workout-based information to interested users. The workout-based information of the professional athletes are collected through the use of wearable devices and stored in a workout-based information network. Interested users (e.g., fans, other professional athletes) may subsequently download workout-based data from one or more professional athletes onto their user device. The workout-based data may be used by the interested users to compare their own personal progress with one or more other professional athletes. It should be noted that the workout-based data is updated in real-time, for example, based on when a particular professional athlete most recently undergoes a workout session. The workout-based data may also be cumulative over time.

Figure 1:
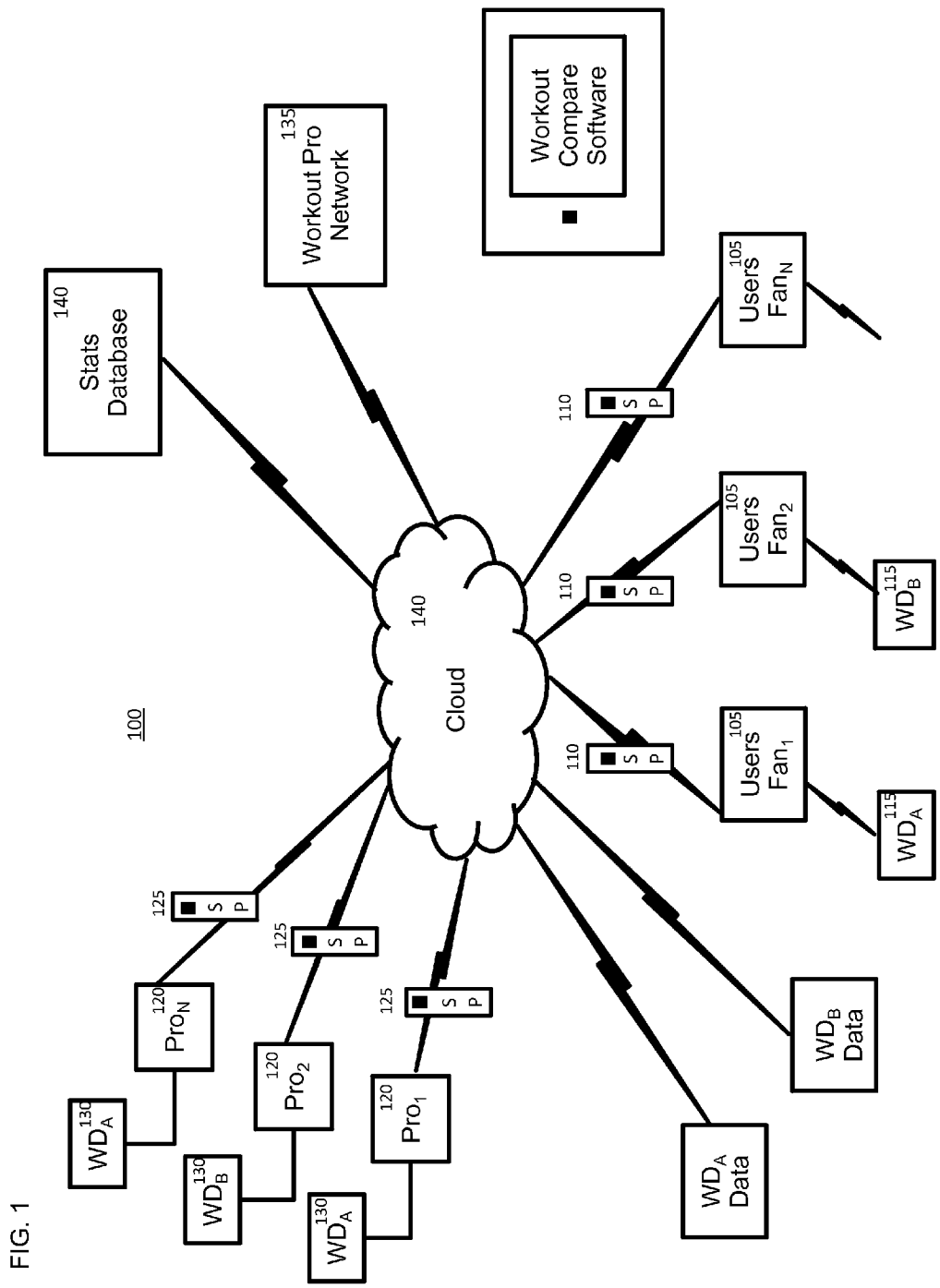
FIG. 1 illustrates a system for sharing workout-based information of professional athletes with interested users.

FIG. 1 illustrates a system 100 for sharing workout-based information of professional athletes with interested users. The system 100 includes a plurality of interested users 105 (e.g., fans) and a plurality of professional athletes. The system 100 also includes databases and networks that are used to facilitate the sharing of workout-based information of professional athletes with interested users. Further details pertaining to the elements of the system 100 are provided below.

As illustrated in FIG. 1, each of the interested users 105 has a corresponding user device 110 (e.g., smartphone). The user devices 110 include one or more applications or programs compatible with the system 100. In particular the user devices 110 would have an application or program (referenced as the workout compare software in FIG. 1) directed at comparing workout-based information of one or more professional athletes with workout-based information of the user 115. As illustrated in the figure, the workout compare software is represented via a black square that can be found within the user device 110. The workout-based information of the user, which is referenced by the workout compare software, may be manually inputted into the user device 110 or obtained through the use of one or more wearable devices 115. The workout-based information can then be compared by the workout compare software in each of the user devices 110 with one or more workout-based information from one or more professional athletes 120 obtained from the workout pro network.

It should be noted that each of the interested users 105 may have one or more wearable devices 115. The wearable devices 115 may be used to obtain health-based sensor data corresponding to relevant workout-based information. For example, when the interested user 105 undergoes a workout session, the wearable device 115 can be used to obtain health-based sensor data (e.g., biometric parameters). The health-based sensor data can be subsequently processed to evaluate the effects of a particular workout session. The wearable devices 115 may be capable of measuring a variety of different biometric parameters belonging to a particular interested user 105 including calories burned and heart-rate/pulse. These wearable devices 115 may be wearable devices that are readily available to the public (e.g., FitBit).

The system 100 also includes a plurality of professional athletes 120. These professional athletes 120 may be professional athletes across any sport (e.g., football, basketball, baseball). It should be noted that each professional athlete may participate in different workout sessions, for example, to maintain or improve on a particular aspect of their performance within their respective sport (e.g., endurance, muscle mass, weight loss). The professional athletes 120 may similarly have user devices 125 (e.g., smart phones) and wearable devices 130 (e.g., BodyMedia, Fitbit) as described above with respect to the interested users 105.

Workout-based information from each of the professional athletes 120 may be obtained from their corresponding wearable devices 130. The workout-based information can then be transmitted to the user device 125 associated with the professional athlete 120. The user device 125 of the professional athlete 120 then connects with the workout pro network 135 and uploads their respective workout-based information into the network 135 for storage. The workout pro network 135 is capable of storing workout-based information of the various professional athletes 120 in a stats database 140. It should be noted that the information provided to the workout pro network 135 and stored in the stats database 140 may be updated on a regular basis (e.g., real-time, hourly, daily). For example, once a workout session has been completed, obtained workout-based information from the professional athlete may be provided to the workout pro network 135 immediately.

Each of the interested users 105 and professional athletes 120 are capable of connecting to the workout pro network 135 to download workout based information. More specifically, the user devices 110, 125 of the interested users 105 and professional athletes 120, respectively are capable of communicating with the workout pro network 135 via the cloud or internet 140. Once connected, for example, the interested user 105 may download workout-based information for one or more professional athletes onto their user device 110. In some embodiments, the interested user 105 may be capable of selecting workout-based information for a particular professional athlete or for a particular group of professional athletes (e.g., workout-based information for basketball players). The workout-based information downloaded into the user device 110 can then be used by the workout compare software to evaluate workout-based information of the user 105 and the professional athlete 125.

It may be possible that vendors/manufacturers that are associated with a particular brand of a wearable device 115, 130 may have the ability to control who can access the workout-based information and when others can access the workout-based information. For example, a vendor/manufacturer may provide selected users (e.g., interested users and/or professional athletes) using their brand of wearable devices early access to workout-based information obtained by the same branded wearable devices of professional athletes. The early access may be associated with a period of time before the workout pro network 135 is capable of updating the stats database 140 with the recently received workout based information of one or more professional athletes.

Figure 2:
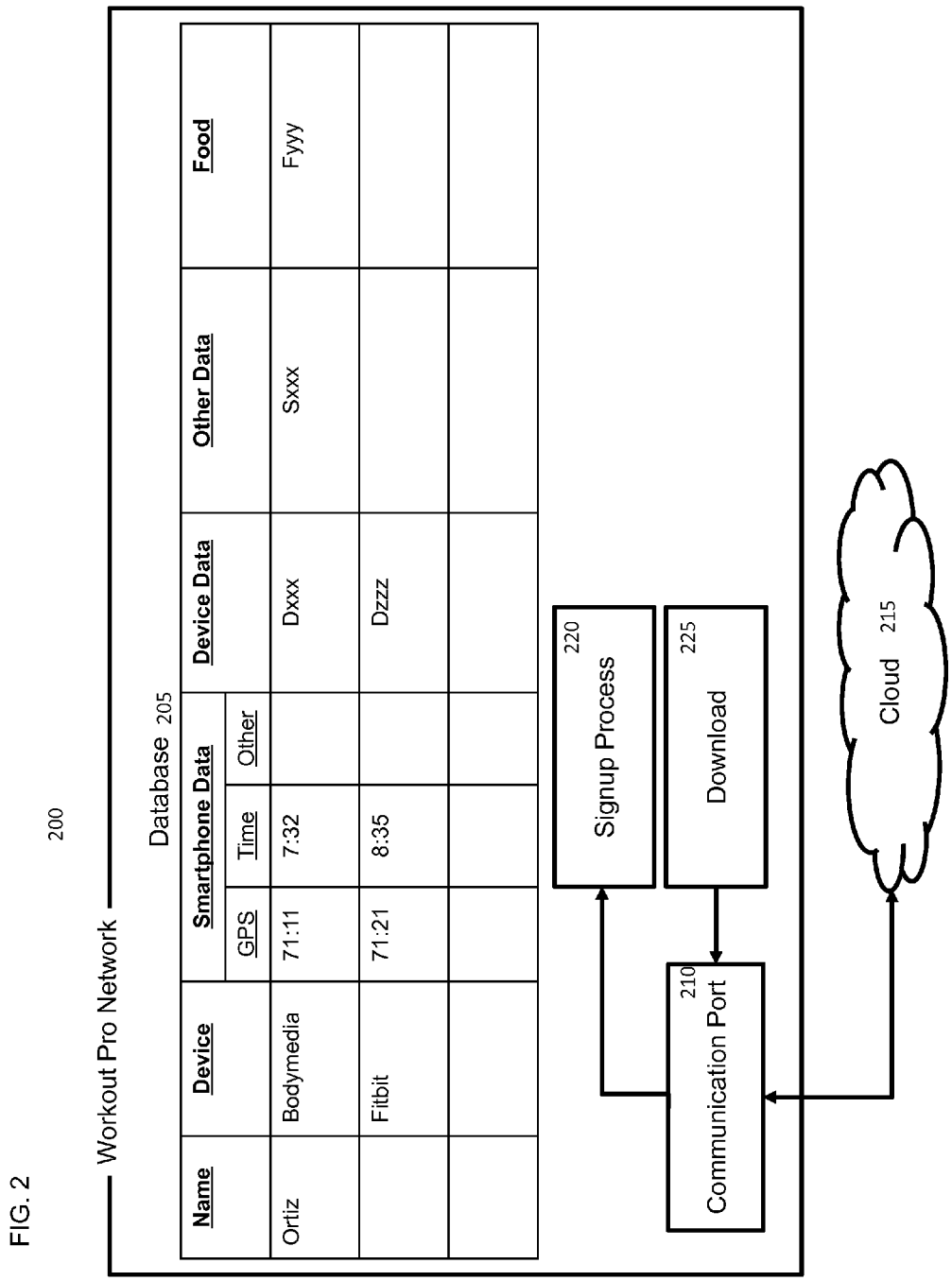
FIG. 2 illustrates the workout pro network and corresponding stats database used to store workout-based information of professional athletes.

FIG. 2 illustrates the workout pro network 200. As illustrated in the figure, the workout pro network 200 includes a database 205, a communication port 210 used to communicate with the internet or cloud 215, a sign-up process 220 and a download process 225. Further details relating to the different elements of the workout pro network 200 are provided below.

The database 205 associated with the workout pro network 200 is a database that includes information (e.g., personal information) about each professional athlete that uploads their respective workout-based information to the workout pro network 205. The information provided from each professional athlete is received by the communication port 210. As illustrated in the figure, the database 205 may include personal information such as their name and what wearable device they are using. Other types of information may also be stored in the database 205 such as information from their user device (e.g., smart phone) including their location (i.e. GPS) and technology the professional athlete is using (e.g., programs, applications). It may be possible that the professional athlete may provide further information to be stored in the database 205 as well, for example, their diet. It should be noted that the information stored in the database 205 of the workout pro network 200 may also be helpful in evaluating the workout-based data between the professional athlete and, for example, the interested user.

The sign-up process 220 facilitates users (e.g., interested users and/or professional athletes) with the use of the workout-based information associated with the workout pro network 200. Generally, users would need to sign-up using the sign-up process 220 (e.g., create an account, user profile). The users may be charged a fee (e.g., one-time, monthly-subscription) for use of the workout pro network 200. The sign-up process 220 may facilitate payment from the user. In some embodiments, the sign-up process 220 can also take as input names of particular professional athletes the user would like to download workout-based information about. The names of the professional athletes may be saved and associated with the user.

After the sign-up process 220, the user is allowed to download workout-based information about one or more pros associated with the workout pro network 200 to their respective user device using the download process 225. The download process may be a manual request performed by the user. In some cases, the user may be allowed to automatically request via the user device updated workout-based information regarding one or more professional athletes on a regular basis. In this case, the download process can provide the requested updated workout-based information without any further action from the user.

Figure 3:
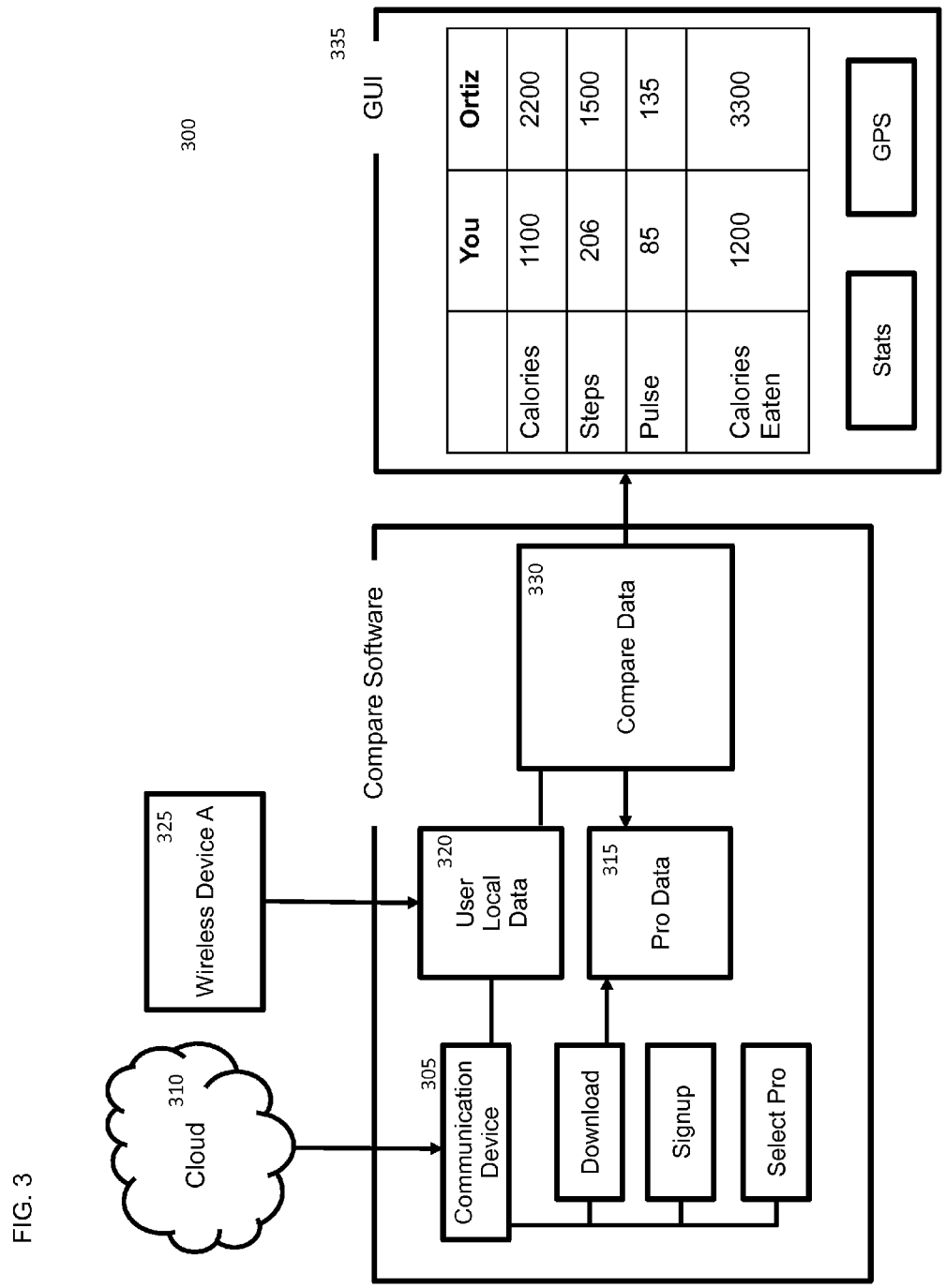
FIG. 3 illustrates the workout compare software.

FIG. 3 illustrates the workout compare software 300. As noted above, the workout compare software 300 is found, for example, in the user devices associated with the interested users and/or the professional athletes. The workout compare software 300 is used to compare workout-based information obtained from a user workout session with workout-based information of one or more professional athletes downloaded from the workout pro network.

As illustrated in the figure, the workout compare software 300 includes a communication device 305. The communication device 305 is connected to the cloud or Internet 310. Through the communication device 305, the workout compare software 300 can obtain workout-based information of one or more professional athletes. The workout-based information of the professional athletes may be stored 315 in the workout compare software 300. The download process, sign-up process and process of selecting one or more professional athletes may also be included in the workout compare software 300 to facilitate the obtaining of desired workout-based information of the one or more professional athletes from the workout pro network.

The workout compare software 300 may also store workout-based information related to the user 320. This workout-based information of the user may be manually inputted into the user interface. In some embodiments, the workout-based information of the user may also be obtained from a corresponding wearable device 325. The wearable device 325 may be any wearable device capable of obtaining health-based sensor data (e.g., biometric parameters) that can be used to evaluate the effect of a workout session.

The workout compare software 300 can then compare the stored workout-based information of the user 320 and one or more professional athletes 315 via the compare data process 330. The compare data process 330 can process and evaluate the stored workout-based information stored in the workout compare software 300 between the user and the professional athlete.

The workout compare software 300 can then output a graphical user interface (GUI) 335 that displays the comparison between the workout-based information of the user and the professional athlete(s) chosen by the user. The GUI 335 may include a table which includes workout-based information of the user and the professional athlete(s) including calories, steps taken, pulse and calorie intake. It should be noted that other types of workout-based information may also be displayed in the GUI 335.

The GUI 335 may include additional features such as stats and GPS. The stats feature may provide further information relating to the workout session of the professional athlete. For example, the stats may provide the duration of the workout session. The GPS (global positioning system) feature may also be included with the GUI 335. The GPS feature may be provided to indicate information about where the particular professional athlete performed the workout session. The GPS feature, for example, may indicate that the professional athlete worked out at a gym. It should be noted that other features may also be included in the GUI 335 that can further provide details and context about workout-based information of one or more athletes.

Figure 4:
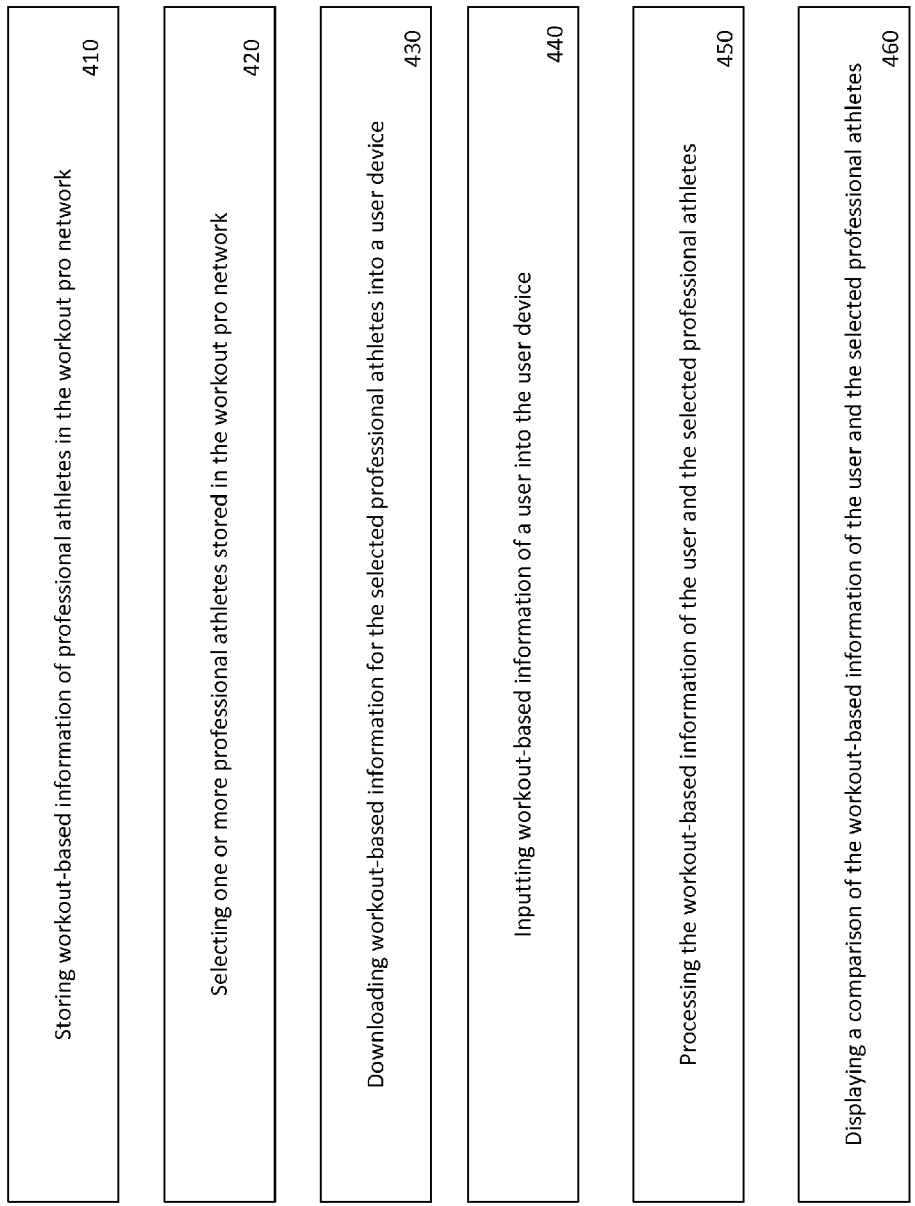
FIG. 4 illustrates a flowchart for the sharing of workout-based information of professional athletes with interested users

FIG. 4 illustrates a flowchart 400 for the sharing of workout-based information of professional athletes with interested users. More specifically, the flowchart illustrates the steps associated with providing the workout-based information from the professional athletes to the workout pro network that will subsequently be downloaded by the interested users for comparison.

In step 410, workout-based information from the various professional athletes are stored in the workout pro network. The workout-based information may be obtained from one or more sensors associated with a wearable device worn by the professional athlete. The sensor data can then be transmitted to the user device associated with the wearable device. The workout-based information may also be manually inputted into the user device of the professional athlete. The workout-based information, once provided to the user device, can transmit the workout-based information to the workout pro network to be stored.

In step 420, the user can select one or more professional athletes having stored workout-based information in the workout pro network to be downloaded. In some embodiments, the user can specify a sport or genre of professional athletes (e.g., football players) and the workout pro network can generate one or more professional athletes for the user to choose.

It should be noted that the user, before being allowed to select desired professional athletes, may be required to sign up and obtain authorization to use the workout pro network. In some cases, a fee (e.g., one-time, monthly subscription) may be required.

In step 430, the user can download the workout-based information of the one or more selected professional athletes from the workout pro network. The workout-based information associated with the one or more selected professional athletes are stored, for example, in the user device of the user. The workout-based information associated with the one or more selected professional athletes will be used to compare with the user workout-based information.

In step 440, the user can provide the workout-based information of the user for the user device to use. The workout-based information can be manually inputted into the user device, for example, through an application, program or GUI. In other embodiments, a wearable device having one or more sensors may obtain sensor data that can be transmitted to the user device and processed into workout-based information. The user workout-based information will be compared with the workout-based information from one or more selected professional athletes.

In step 450, the user device (i.e. the workout compare software) processes the workout-based information of the user and the selected one or more professional athletes. The workout compare software can also evaluate health-based data of the user and the professional athletes and determine the relative effects of the workouts for the user and the professional athlete.

In step 460, the output of the evaluation performed in step 450 is displayed for the user to view. The output may be displayed, for example, via a graphical user interface on the user device. The information detailing the comparison between the workout-based information of the user and the selected one or more professional athletes may be displayed via a graph, chart or any other possible way of illustrating a comparison between the various data sets.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claim.

It should be noted that the technology can be used in a variety of different events and venues including entertainment or cultural events presented at a theater, gymnasium, stadium or other facility involving a group of people. Such events may also include a variety of sporting events such as football (American and global), baseball, basketball, soccer, ice hockey, lacrosse, rugby, cricket, tennis, track and field, golf, cycling, motor sports such as automobile or motorcycle racing, horse racing, Olympic games, and the like; cultural events such as concerts, music festivals, plays, or the opera, and the like; religious events; and more permanent exhibitions such as museums or historic homes.

What is claimed is:

1. A method for comparing user workout information and professional athlete workout information, the method comprising:
   storing professional athlete workout information in a professional athlete workout database, the professional athlete workout information associated with one or more professional athletes;
   receiving a selection from a user device, the selection identifying a set of selected professional athletes, the set of selected professional athletes including at least a subset of the one or more professional athletes associated with the professional athlete workout database, the set of selected professional athletes corresponding to a set of selected professional athlete workout information that includes at least a subset of the stored professional athlete workout information;
   retrieving the set of selected professional athlete workout information from the professional athlete workout database, the set of selected professional athlete workout information including at least a subset of the professional athlete workout information corresponding to the set of selected professional athletes;
   receiving user workout information from the user device;
   generating a comparison visualization identifying one or more differences between the user workout information and the set of selected professional athlete workout information; and
   transmitting at least the comparison visualization to the user device, thereby displaying at least the comparison visualization at the user device.

2. The method of claim 1, wherein the professional athlete workout information includes sensor-based professional athlete data received from one or more professional athlete wearable devices and is recorded by one or more sensors associated with the one or more professional athlete wearable devices, the one or more professional athlete wearable devices having been worn by at least a subset of the one or more professional athletes.

3. The method of claim 1, wherein the professional athlete workout information includes manual-input-based professional athlete data received from the user device after being received by the user device via manual input.

4. The method of claim 1, wherein the user workout information includes sensor-based user data obtained via one or more sensors associated with one or more wearable devices that transmitted the data to the user device, the one or more wearable devices having been worn by a user associated with the user device.

5. The method of claim 1, wherein the user workout information includes manual-input-based user data input received by the user device via manual input.

6. The method of claim 1, wherein the comparison visualization is one of a chart or a graph.

7. A system for comparing user workout information and professional athlete workout information, the system comprising:
   a memory storing at least a professional athlete workout database that includes professional athlete workout information associated with one or more professional athletes;
   a communication transceiver in communicative contact with at least a user device; and
   a processor coupled to the memory and to the communication transceiver, wherein execution of instructions stored in the memory by the processor:
     receives the selection from the user device, the selection identifying a set of selected professional athletes, the set of selected professional athletes including at least a subset of the one or more professional athletes associated with the professional athlete workout database, the set of selected professional athletes corresponding to a set of selected professional athlete workout information that includes at least a subset of the stored professional athlete workout information,
     retrieves the set of selected professional athlete workout information from the professional athlete workout database, the set of selected professional athlete workout information including at least a subset of the professional athlete workout information corresponding to the set of selected professional athletes;
     receives user workout information from the user device,
     generates a comparison visualization identifying one or more differences between the user workout information and the set of selected professional athlete workout information, and
     transmits at least the comparison visualization to the user device, thereby displaying at least the comparison visualization at the user device.

8. The system of claim 7, wherein the professional athlete workout information includes sensor-based professional athlete data received from one or more professional athlete wearable devices and is recorded by one or more sensors associated with the one or more professional athlete wearable devices, the one or more professional athlete wearable devices having been worn by at least a subset of the one or more professional athletes.

9. The system of claim 7, wherein the professional athlete workout information includes manual-input-based professional athlete data received from the user device after being received by the user device via manual input.

10. The system of claim 7, wherein the user workout information includes sensor-based user data obtained via one or more sensors associated with one or more wearable devices that transmitted the data to the user device, the one or more wearable devices having been worn by a user associated with the user device.

11. The system of claim 7, wherein the user workout information includes manual-input-based user data input received by the user device via manual input.

12. The system of claim 7, wherein the comparison visualization is one of a a chart or a graph.

13. A non-transitory computer-readable storage medium, having embodied thereon a program executable by a processor to perform a method for comparing user workout information and professional athlete workout information, the method comprising:
   storing professional athlete workout information in a professional athlete workout database, the professional athlete workout information associated with one or more professional athletes;
   receiving a selection from a user device, the selection identifying a set of selected professional athletes, the set of selected professional athletes including at least a subset of the one or more professional athletes associated with the professional athlete workout database, the set of selected professional athletes corresponding to a set of selected professional athlete workout information that includes at least a subset of the stored professional athlete workout information;

retrieving the set of selected professional athlete workout information from the professional athlete workout database, the set of selected professional athlete workout information including at least a subset of the professional athlete workout information corresponding to the set of selected professional athletes;

receiving user workout information from the user device;

generating a comparison visualization identifying one or more differences between the user workout information and the set of selected professional athlete workout information; and transmitting at least the comparison visualization to the user device, thereby displaying at least the comparison visualization at the user device.

\* \* \* \* \*